(12) United States Patent
DeCato et al.

(10) Patent No.: US 6,488,902 B1
(45) Date of Patent: Dec. 3, 2002

(54) STERILIZER EXHAUST GAS INACTIVATION

(75) Inventors: Kevin DeCato, Dana Point; Dan Smith, Irvine; Jim Kohler, Laguna Hills; Paul Jacobs, Dove Canyon, all of CA (US)

(73) Assignee: Ethicon, Inc., Somerville, NJ (US)

( * ) Notice: Subject to any disclaimer, the term of this patent is extended or adjusted under 35 U.S.C. 154(b) by 63 days.

(21) Appl. No.: 09/181,426

(22) Filed: Oct. 28, 1998

Related U.S. Application Data

(60) Provisional application No. 60/064,048, filed on Nov. 3, 1997.

(51) Int. Cl.[7] .............................................. B01D 53/46
(52) U.S. Cl. ...................... 423/210; 423/245.1; 422/30
(58) Field of Search ........................... 422/30; 423/210, 423/584, 579, 245.1

(56) References Cited

U.S. PATENT DOCUMENTS

| | | | | |
|---|---|---|---|---|
| 3,492,093 A | * | 1/1970 | Start et al. .................. | 423/579 |
| 3,912,451 A | * | 10/1975 | Gaglia, Jr. ..................... | 21/58 |
| 4,643,876 A | * | 2/1987 | Jacobs et al. ................. | 422/23 |
| 4,756,882 A | * | 7/1988 | Jacobs et al. ................. | 422/23 |
| 4,909,999 A | | 3/1990 | Cummings et al. .......... | 422/298 |
| 5,015,442 A | | 5/1991 | Hirai ............................ | 422/121 |
| 5,069,880 A | | 12/1991 | Karlson ................. | 422/186.19 |
| 5,087,419 A | | 2/1992 | Lutz ............................. | 422/28 |
| 5,102,634 A | * | 4/1992 | Hayashi et al. .............. | 423/210 |
| 5,120,512 A | | 6/1992 | Masuda ....................... | 422/297 |
| 5,229,071 A | * | 7/1993 | Meo, III ......................... | 422/2 |
| 5,334,355 A | | 8/1994 | Faddis ......................... | 422/122 |

FOREIGN PATENT DOCUMENTS

| | | | | |
|---|---|---|---|---|
| EP | 0 110 609 A1 | * | 6/1984 | .................. 422/30 |
| WO | WO 97/34682 | | 9/1997 | |

* cited by examiner

*Primary Examiner*—Steven P. Griffin
*Assistant Examiner*—Timothy C Vanoy

(57) ABSTRACT

A process is provided for removing hydrogen peroxide and oil out the exhaust gas emitted from a sterilization chamber, such as from a STERRAD® medical instrument sterilizer. The exhaust gas is passed through either alumina or a mass of metal wool, which sorbs the lubricating oil out of the exhaust gas, and then through alumina coated with a precious metal catalyst, such as Pd, Pt, Rh and alloys and compounds thereof, which decomposes the hydrogen peroxide into water and oxygen. The precious metal coating on the alumina may be sufficiently discontinuous to allow residual lubricating oil in the exhaust gas to be sorbed into the alumina.

17 Claims, 6 Drawing Sheets

STERILIZER EXHAUST GAS INACTIVATION

This application claims priority from provisional application No. 60/064,048 filed Nov. 3, 1997.

FIELD OF THE INVENTION

The present invention relates to a method and device for reducing the percentage of hydrogen peroxide in gas exhausting from a sterilization chamber containing hydrogen peroxide vapor.

BACKGROUND OF THE INVENTION

A very common method for sterilizing medical instruments and devices comprises contacting the instruments and devices with vapor phase hydrogen peroxide. Several systems are available commercially to effect such sterilization, such as the STERRAD® Sterilization Systems available from Advanced Sterilization Products division of Johnson & Johnson Medical of Irvine, Calif. In general, such sterilization systems comprise a chamber into which the instruments to be sterilized are placed. Air within the chamber is evacuated and hydrogen peroxide in the vapor phase is admitted to the chamber. Some systems, such as the STERRAD®, additionally induce a plasma upon the hydrogen peroxide sterilization gases. This enhances the sterilization and has the added benefit of disassociating the hydrogen peroxide molecules such that when the hydrogen peroxide plasma returns to its gaseous state, the molecules recombine to form simple oxygen and water vapor thereby lessening the need to deactivate the hydrogen peroxide before exhausting it from the sterilization chamber into the-environment.

Some systems forego the plasma and merely rely upon the hydrogen peroxide vapor to effect sterilization. A common practice for such systems, is to vent their exhaust to a vent exterior of the room housing the sterilizer, typically to a vent pipe on the roof. Little or no attempt is made to chemically alter the hydrogen peroxide and it leaves the vent in active form. A drain may be provided to collect any liquid hydrogen peroxide. Such a venting system inhibits movement of the sterilizer making it impractical to move between laboratories etc. as the vent requires the sterilizer to remain at a fixed location.

Even with most or all of the hydrogen peroxide being broken down by induction of a plasma, it is desirable to provide some means to deactivate hydrogen peroxide. For instance, the admission of hydrogen peroxide raises the pressure within the chamber and it is often desirable to further evacuate the chamber to lower the pressure. The evacuated gasses will thus contain a concentration of hydrogen peroxide. The STERRAD® sterilization system currently available employs a filter comprising copper wool over which gases being exhausted from the chamber are passed. Copper is a well-known catalyst for hydrogen peroxide, although a rather inefficient one. The contact between the hydrogen peroxide and the copper wool tends to break down at least a portion of any hydrogen peroxide exhausting from the chamber into water and oxygen.

SUMMARY OF THE INVENTION

Applicants have developed an improved method and devices for reducing hydrogen peroxide emissions from such a sterilization chamber.

A method, according to the present invention, is provided for cleaning gas exhausting from a chamber which contains a chamber gas comprising hydrogen peroxide. Gas exhausting from the chamber passes along a flow path from the chamber to an exit port. A bed of members coated with a precious metal catalyst for hydrogen peroxide is disposed within the flow path and the exhaust gas passes over the members and catalytically reacts therewith to convert the hydrogen peroxide to water and oxygen. Thus, the exhaust gas reaching the exit has a substantially reduced amount of hydrogen peroxide compared to the chamber gas. Preferably, the precious metal catalyst is selected from the group consisting of palladium, platinum, rubidium and compounds and alloys thereof.

Preferably, a vacuum pump is used to exhaust gas from the chamber. The bed may be located between the vacuum pump and the exit. If so, the members are preferably comprised of alumina, and more preferably the coating of precious metal catalyst on the members is sufficiently discontinuous to allow lubricating oil entrained within the exhaust gases to be absorbed into the alumina members whereby the amount of any such entrained lubricating oil available to deposit upon the catalyst and reduce an available surface area thereof is reduced. These members are preferably substantially spherical, although ovoid or other smooth shapes are desirable. When located downstream of the vacuum pump undue turbulence of the flow may enhance distribution of any entrained lubricating oil from the pump and hasten poisoning of the catalyst. A mass of metal wool disposed within the flow path upstream and adjacent the bed entraps within the wool oil entrained in the exhaust gas and diffuses the exhaust gas to enhance its distribution through the bed. Further, a portion of the bed adjacent the wool can be provided with alumina or other oil absorbent members without the precious metal coating to absorb entrained oil before it reaches the catalyst.

The bed can also be disposed between the chamber and the vacuum pump. The members may be provided with bores therethrough so that the exhaust gas flows through the bores to induce and enhance turbulence thereby enhancing the catalytic reaction. Preferably, such members are tubular. These members may be formed of a polymer such as polyethylene with the catalyst thereon.

A converter, according to the present invention, for cleaning gas exhausting from a chamber comprises a casing having a gas flow path therethrough, the flow path extending to an exit port on the casing. A connector on the casing connects to the chamber whereby gas exhausting from the chamber flows through the flow path. A bed of members coated with a precious metal catalyst for hydrogen peroxide is disposed within the flow path whereby hydrogen peroxide in gas exhausting from the chamber catalytically reacts with the catalyst to convert the hydrogen peroxide to water and oxygen.

DETAILED DESCRIPTION OF THE INVENTION

Figure 1:
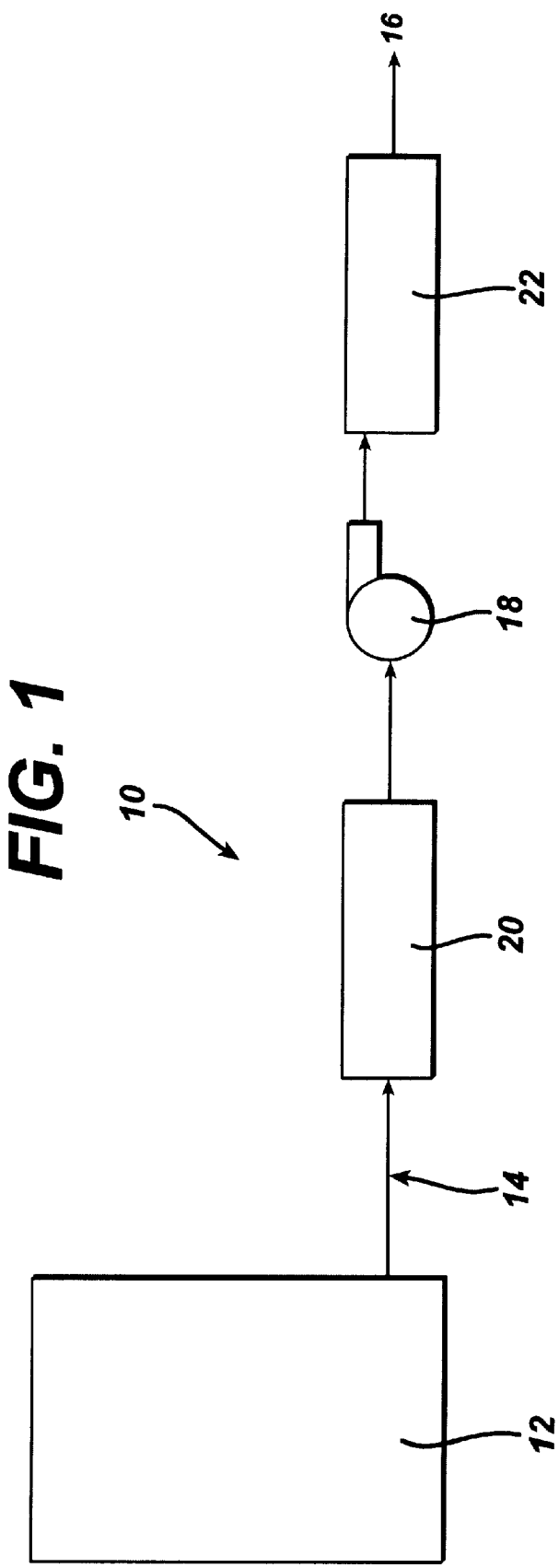
FIG. 1 is a block diagram of a sterilization system employing the method and device for cleaning sterilizer gases according to the present invention.

FIG. 1 discloses in diagram form a sterilization system 10 comprising a sterilization chamber 12 having a flow path 14 from the sterilization chamber 12 to an exit 16. Typically, the exit 16 exhausts to atmosphere within a room containing the sterilization system 10. It is thus desired to reduce or eliminate hydrogen peroxide in the gases exhausting from the exit 16. A vacuum pump 18 draws gases from the sterilization chamber 12 and passes them out through the exit 16.

During a typical sterilization cycle, instruments to be sterilized (not shown) are placed within the sterilization chamber 12 and the vacuum pump 18 exhausts gases within the sterilization chamber 12 to reduce the pressure therein down to 0.5 Torr or below. Hydrogen peroxide is then admitted to the chamber 12. The admission of hydrogen peroxide will somewhat increase the pressure within the sterilization chamber 12, typically back to around 10 Torr. To enhance vaporization of the hydrogen peroxide, to enhance penetration of the vapor into crevices in any items to be sterilized, and if a plasma is desired, to ensure its proper ignition upon inducement of an electromagnetic field, it is desirable to reduce the pressure in the chamber 12 back to the level prior to admission of hydrogen peroxide by exhausting additional gases with the vacuum pump 18. Such exhausted gases, although small in quantity, will contain highly concentrated hydrogen peroxide. Typically on the order of 59% hydrogen peroxide or higher.

An upstream catalytic converter 20, in the flow path 14 upstream of the vacuum pump 18, and a downstream catalytic converter 22, in the flow path 14 downstream of the vacuum pump 18, catalytically act upon any hydrogen peroxide in gases passing along the flow path 14 to reduce or eliminate the hydrogen peroxide by the time such gases reach the exit 16. Although both the upstream and downstream catalytic converters 20 and 22 may be employed together, suitable hydrogen peroxide reduction can be effected with either one thereby eliminating the need and expense to employ two catalytic converters.

Figure 2:
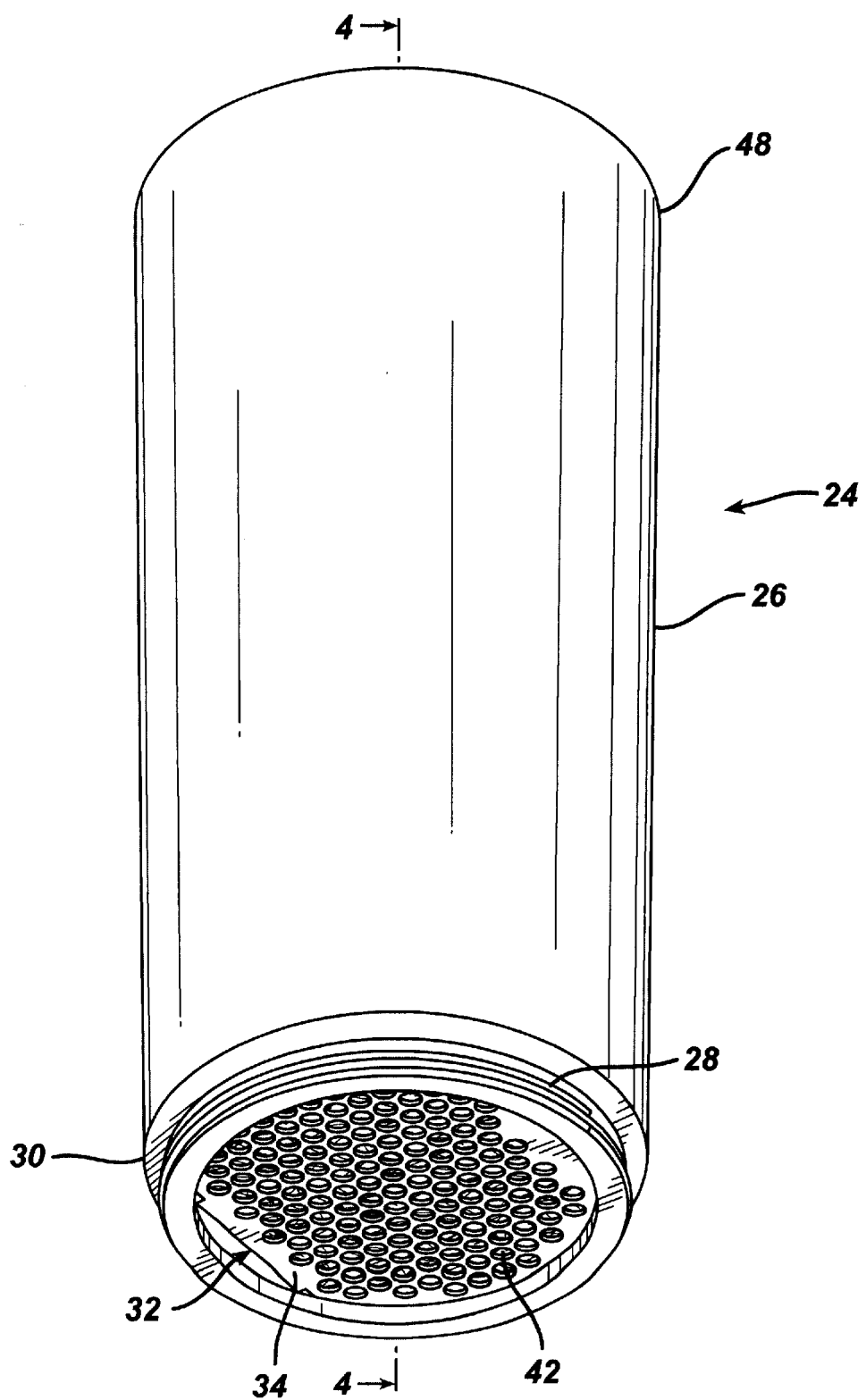
FIG. 2 is a perspective view of an embodiment of the device of FIG. 1 located downstream of the pump.
Figure 3:
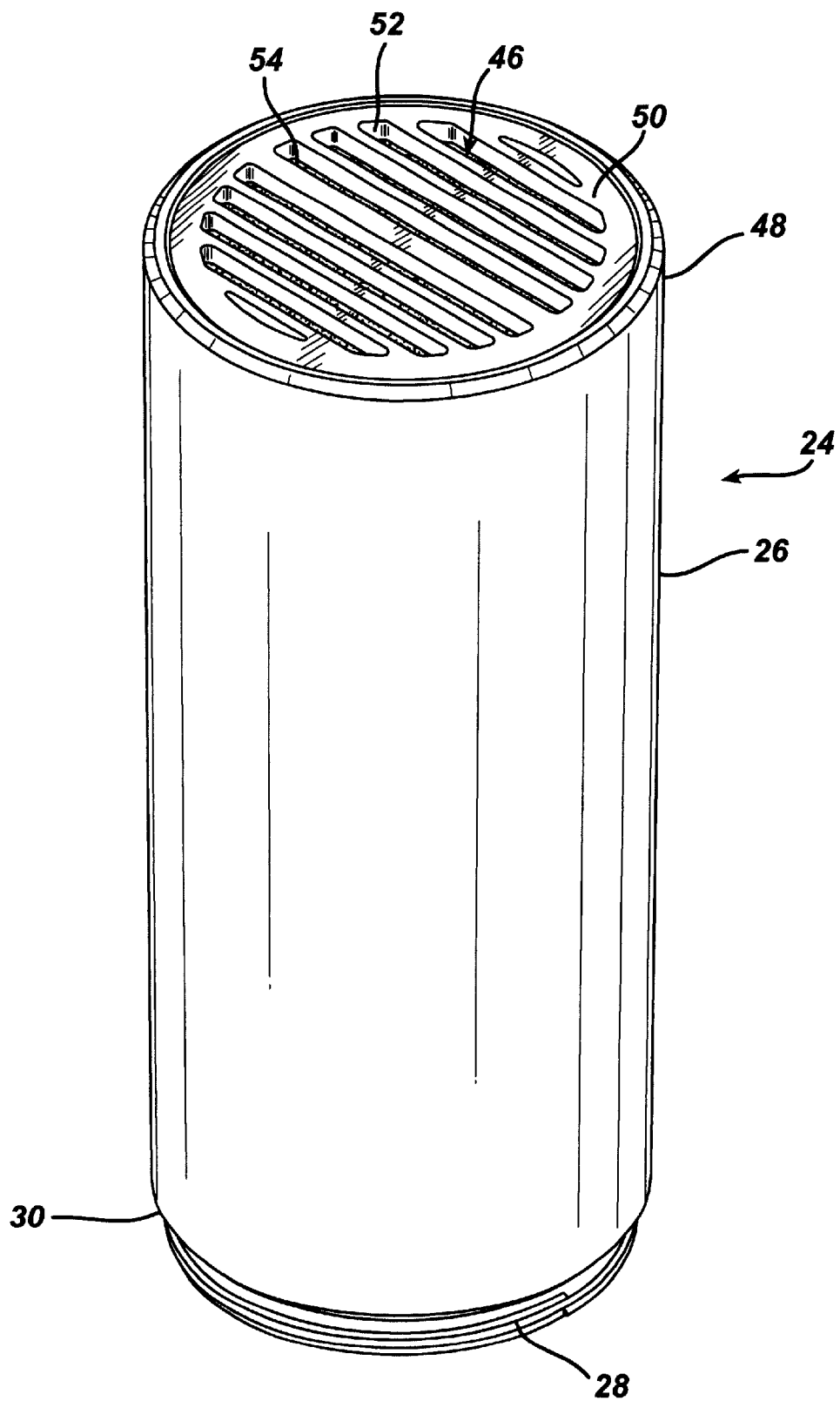
FIG. 3 is a further perspective view of the device of FIG. 2.

FIGS. 2 and 3 depict a downstream catalytic converter cartridge 24 corresponding to the catalytic converter 22. The cartridge 24 comprises a cylindrical body 26 having a male threaded connection 28 at a first end 30 thereof to allow removable connection to the sterilization system 10 (see FIG. 1) thereby facilitating removal and replacement of the cartridge 24. Preferably, the body 30 is formed of an inexpensive easy to form polymeric material which is compatible with hydrogen peroxide, such as polyvinyl chloride (PVC), although other suitable materials such as aluminum will be apparent to those of skill in the art.

Figure 4:
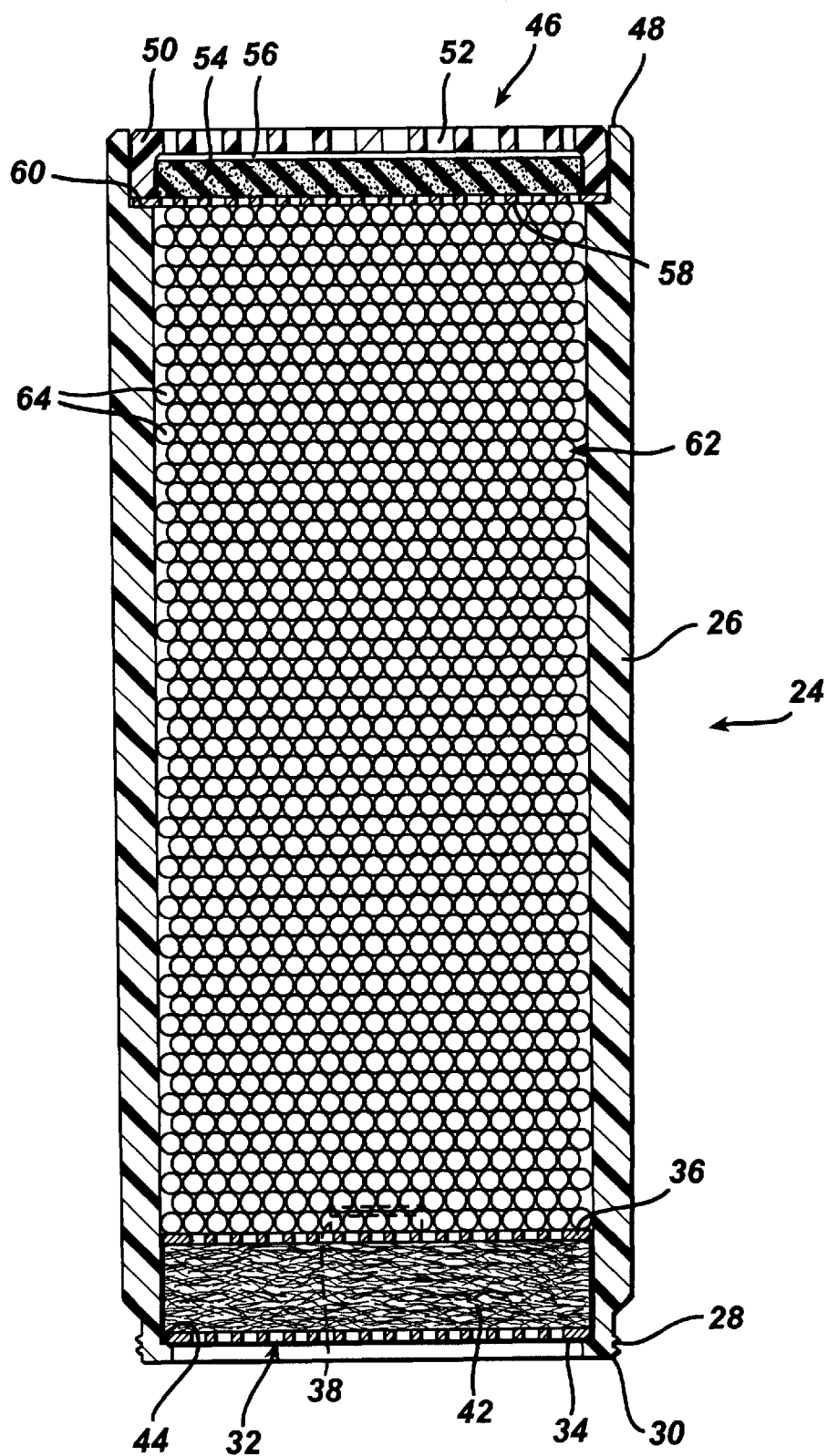
FIG. 4. is a sectional view taken along lines 4—4 of FIG. 2.
Figure 5:
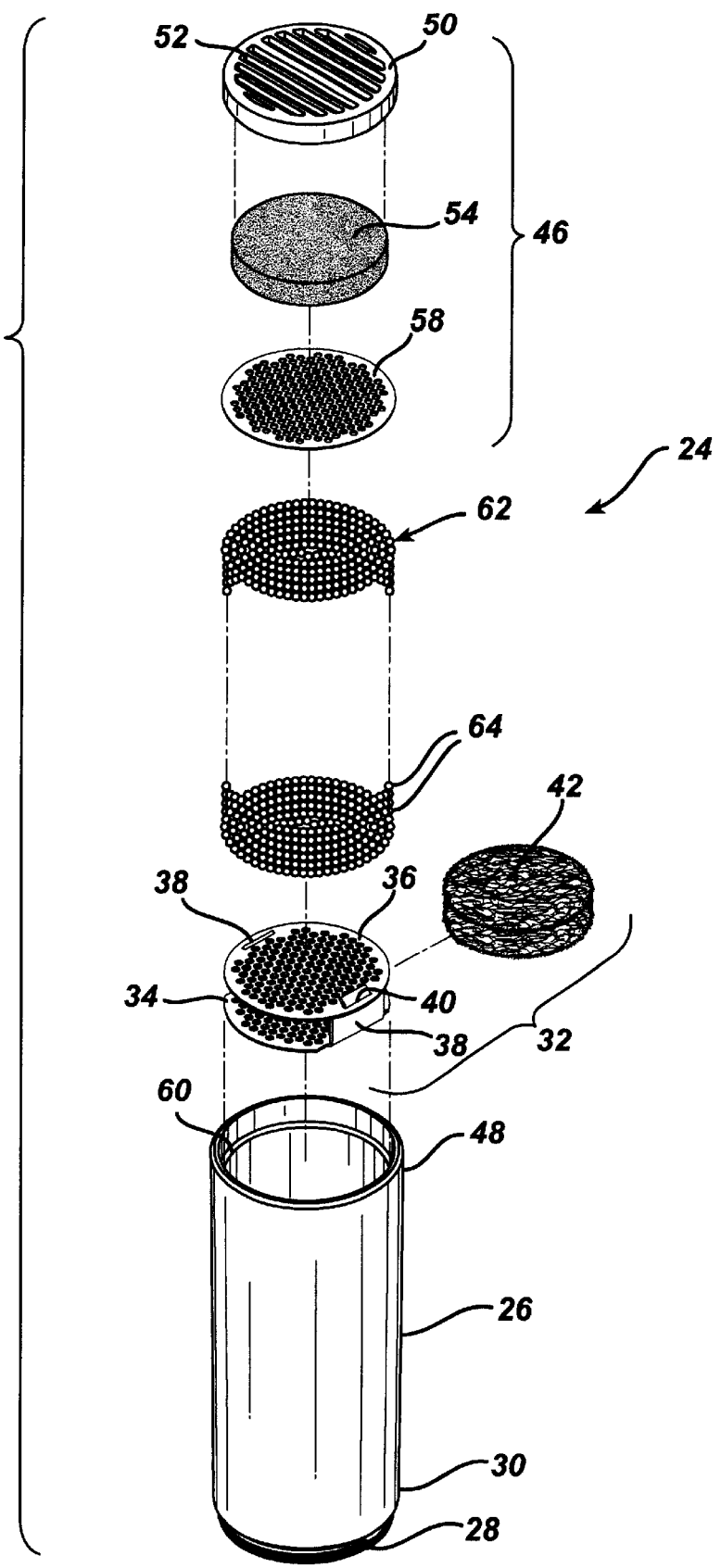
FIG. 5 is an exploded perspective view of the device of FIG. 2.

Turning also to FIGS. 4 and 5, an inlet filter 32 is positioned within the cylindrical body 26 at the first end 30. The inlet filter 32 comprises first and second perforated discs 34 and 36 held in parallel spaced relations by tabs 38 extending from the first disc 34 and received within slots 40 in the second disc 36.

Preferably, the discs 34 and 36 are formed of aluminum. Aluminum wool filter material 42 resides between the first and second discs 34 and 36. A lip 44 at the cylindrical 401 body first end 30 holds the inlet filter 32 in the proper position.

An exit filter 46 is positioned at a second end 48 of the cylindrical body 26. It comprises a discoidal cap 50 preferably formed of PVC, having a plurality of parallel, elongated slots 52 therethrough. A disc of particulate filtering foam 54 sits within a recess 56 in the cap 50 inwardly of and adjacent the slots 52. If desired, activated charcoal may also be employed to help reduce odor emissions from the sterilizer. A perforated aluminum disc 58 covers the recess 56 to hold the foam 54 within the cap 50. The exit filter 46 abuts a lip 60 within the body 26 and is adhered therein with an appropriate adhesive.

A filter bed 62, comprising a plurality of alumina spheres 64 coated with palladium, fills the body 26 between the inlet and exit filters 32 and 46. Preferably, the spheres are comprised of 0.5% Pd/alumina, type SOB having a diameter of between 2 and 4.75 millimeters, a metal area of 10 $m^2$/g, an apparent bulk density of 0.75 $g/cm^2$ and a pore volume of 0.45 $cm^2$/g.

In operation, exhaust gases enter the downstream catalytic converter 22 at the first end 30 passing through the inlet filter 32, where the aluminum wool filter 42 traps lubricating oil which may be contained in the exit stream from the vacuum pump 18. Vacuum pumps are typically provided with efficient epoxy glass microfiber filter elements to trap and recycle entrained lubricating oil in their exit flow, and it is recommended that to avoid poisoning of the palladium catalyst that the oil removing capacity of the standard filter be increased by a factor of 2 or more until no visually apparent oil mist is deposited on parts downstream of the vacuum pump.

The aluminum wool filter 42 provides a measure of added protection for the filter bed 62. It is not thought that oil chemically interacts with the palladium coating of the spheres 64, but rather may occlude portions thereof to reduce the effective surface area which may catalytically react with gases passing through the filter bed 62. The filter 42 also acts as a diffuser to more efficiently distribute the exhaust gases through the filter bed 62.

As the gases leave the inlet filter 32, they pass over the filter bed 62 to come into intimate contact with the palladium coated spheres 64. Any hydrogen peroxide in the gases tends to catalytically react with the palladium, breaking down into simple oxygen and water vapor. No heating of the catalyst is required. The flow then passes through the exit filter 46 and out to the environment.

Figure 6:
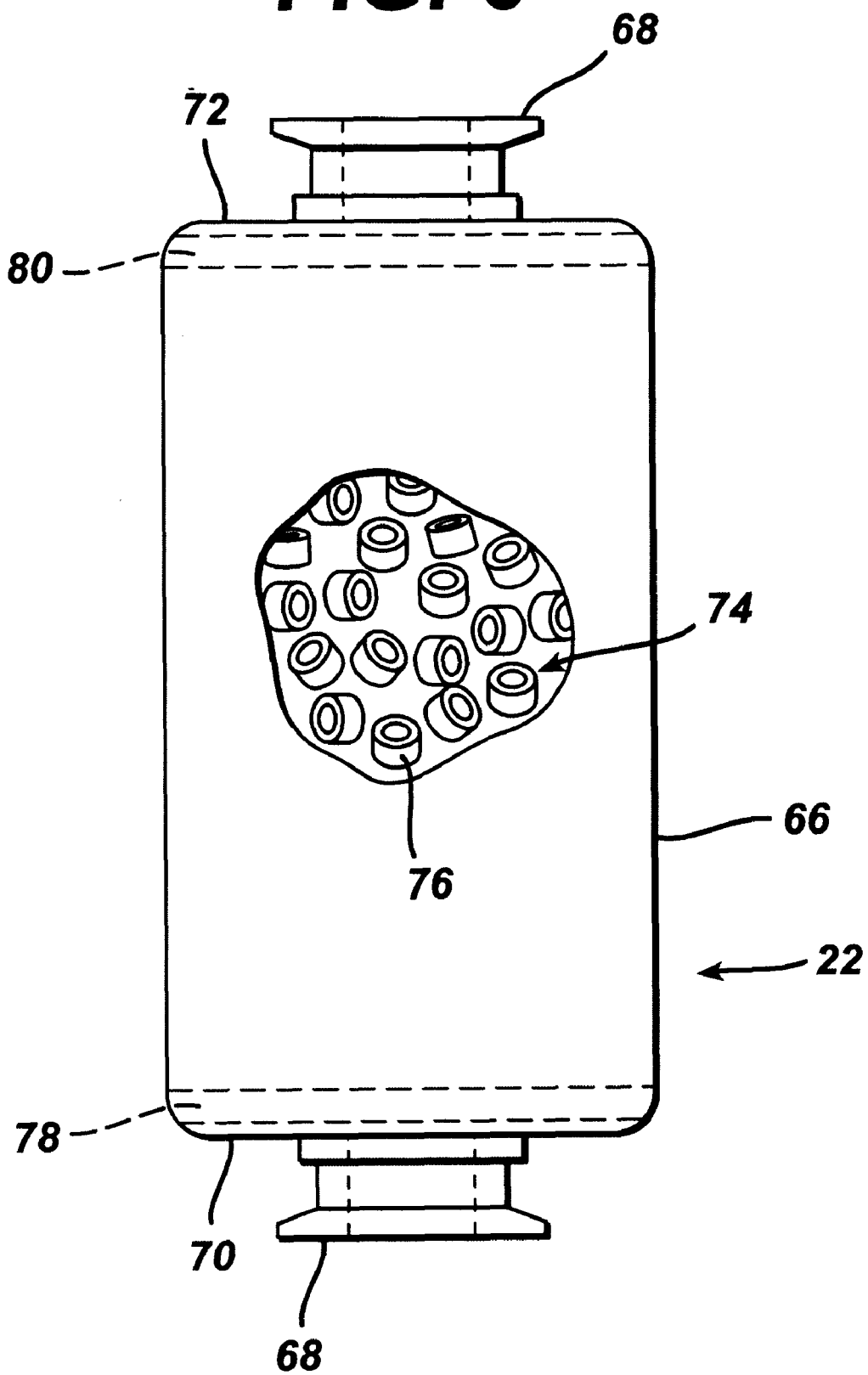
FIG. 6 is a front elevational view of an alternative embodiment of the device of FIG. 1 located upstream of the pump.

FIG. 6 depicts the upstream converter 20 (see also FIG. 1). It comprises a body 66 having connections 68 at its first and second ends 70 and 72 and a bed 74 of tubular members 76 coated with platinum. The members 76 are shown loosely packed for clarity, but in practice it is preferable to pack the members 76 closely within the body 66. A pair of screens 78 and 80 hold the members 76 within the body 66. The screens function similarly to their counterparts 32 and 46 in the downstream converter 22 (see also FIG. 5), but the inlet screen 78 need not filter entrained oil as the converter 20 is positioned upstream of the pump 18.

The members preferably are formed of polyethylene, are 6 mm long, have in internal diameter of 6 mm, and an external diameter of 10 mm. The platinum can be coated onto the members 76 using platinum dissolved in a salt and acid solution. Such a service is provided by Johnson Matthey of 2001 Nolte Drive, West Deptford, N.J.

The tubular shape of the members enhances turbulence of the flow through the bed 74. Due to the turbulence, performance of this type of bed 74 per unit surface area of catalyst exceeds that of the bed 62 of spherical members 64.

While the invention has been particularly described in connection with specific embodiments thereof, it is to be understood that this is by way of illustration and not of limitation, and that the scope of the appended claims should be construed as broadly as the prior art will permit

What is claimed is:

1. A method of cleaning gas exhausting from a chamber; the method comprising the steps of:

exhausting an exhaust gas which comprises hydrogen peroxide from the chamber along a flow path from the chamber to an exit port;

passing the exhaust gas through oil absorbent media not coated with precious metal catalyst, thereby sorbing entrained lubricating oil out the exhaust gas;

passing the exhaust gas over a bed of members disposed within the flow path, the members comprising alumina and being coated with a precious metal catalyst for hydrogen peroxide; and catalytically reacting hydrogen peroxide in the exhaust gas with the catalyst to convert said hydrogen peroxide to water and oxygen;

whereby the exhaust gas reaching the exit has a substantially reduced amount of hydrogen peroxide compared to the chamber gas.

2. A method according to claim 1 wherein the precious metal catalyst is selected from the group consisting of palladium, platinum, rubidium and compounds and alloys thereof.

3. A method according to claim 1 wherein the step of exhausting the exhaust gas from the chamber comprises pumping the exhaust gas from the chamber with a vacuum pump in the flow path.

4. A method according to claim 3 wherein the bed is located between the vacuum pump and the exit.

5. A method according to claim 3 wherein the bed is disposed between the chamber and the vacuum pump.

6. A method according to claim 5 wherein the members are formed of a polymer.

7. A method according to claim 6 wherein the polymer is polyethylene.

8. A method according to claim 1 wherein the coating of precious metal catalyst on the members is sufficiently discontinuous to allow lubricating oil entrained within the exhaust gases to be absorbed into the alumina members whereby the amount of any such entrained lubricating oil available to deposit upon the catalyst and reduce an available surface area thereof is reduced.

9. A method according to claim 8, wherein the oil absorbent media comprises alumina members not coated with the precious metal catalyst, thereby to absorb entrained oil from the exhaust gases.

10. A method according to claim 8, wherein the oil absorbent media comprises metal wool.

11. A method according to claim 1 wherein the members are substantially spherical.

12. A method of cleaning gas exhausting from a chamber; the method comprising the steps of:

exhausting an exhaust gas which comprises hydrogen peroxide from the chamber along a flow path from the chamber to an exit port;

passing the exhaust gas through oil absorbent media not coated with precious metal catalyst, thereby sorbing entrained lubricating oil out of the exhaust gas;

passing the exhaust gas over a bed of members disposed within the flow path, the members being coated with a precious metal catalyst for hydrogen peroxide; and catalytically reacting hydrogen peroxide in the exhaust gas with the catalyst to convert said hydrogen peroxide to water and oxygen;

whereby the exhaust gas reaching the exit has a substantially reduced amount of hydrogen peroxide compared to the chamber gas; and wherein the members have bores therethrough and wherein the exhaust gas flows through the bores to induce and enhance turbulence thereby enhancing the catalytic reaction.

13. A method according to claim 12 wherein the members are tubular.

14. A method according to claim 12 wherein the precious metal catalyst is selected from the group consisting of palladium, platinum, rubidium and compounds and alloys thereof.

15. A method according to claim 12 wherein the step of exhausting the exhaust gas from the chamber comprises pumping the exhaust gas from the chamber with a vacuum pump in the flow path.

16. A method according to claim 15 wherein the bed is located between the vacuum pump and the exit.

17. A method according to claim 12, wherein the oil absorbent media comprises alumina members.

* * * * *